(12) United States Patent
Brown et al.

(10) Patent No.: US 8,785,389 B2
(45) Date of Patent: Jul. 22, 2014

(54) POLYMERIC COLLAGEN BIOMATERIALS

(75) Inventors: Robert Brown, Stanmore (GB); Burcak Alp, Stanmore (GB); Hector Hadjipanayi, Stanmore (GB)

(73) Assignee: UCL Business PLC, London (GB)

( * ) Notice: Subject to any disclaimer, the term of this patent is extended or adjusted under 35 U.S.C. 154(b) by 284 days.

(21) Appl. No.: 13/384,390

(22) PCT Filed: Jul. 16, 2010

(86) PCT No.: PCT/GB2010/001361
§ 371 (c)(1),
(2), (4) Date: Jan. 17, 2012

(87) PCT Pub. No.: WO2011/007152
PCT Pub. Date: Jan. 20, 2011

(65) Prior Publication Data
US 2012/0134949 A1    May 31, 2012

(30) Foreign Application Priority Data
Jul. 16, 2009   (GB) .................................. 0912399.3

(51) Int. Cl.
*A61K 38/39* (2006.01)
*A61K 38/00* (2006.01)

(52) U.S. Cl.
USPC .................... 514/17.2; 514/772.3; 514/788.1; 514/278.1; 514/774; 530/356

(58) Field of Classification Search
CPC ...... A61K 38/014; A61K 35/35; A61K 38/39
See application file for complete search history.

(56) References Cited

U.S. PATENT DOCUMENTS

| | | | | |
|---|---|---|---|---|
| 5,171,574 A | * | 12/1992 | Kuberasampath et al. ... | 424/423 |
| 5,610,148 A | * | 3/1997 | Brown .......................... | 424/445 |
| 5,629,287 A | * | 5/1997 | Brown et al. ................... | 514/8.1 |
| 8,343,758 B2 | * | 1/2013 | Cheema et al. ............... | 435/325 |
| 8,435,552 B2 | * | 5/2013 | O'Brien et al. ............... | 424/423 |
| 8,580,564 B2 | * | 11/2013 | Brown et al. .................. | 435/377 |
| 2006/0121609 A1 | * | 6/2006 | Yannas et al. ................. | 435/395 |
| 2007/0117176 A1 | * | 5/2007 | Aishwarya et al. .......... | 435/68.1 |
| 2008/0138381 A1 | * | 6/2008 | Li et al. ......................... | 424/423 |
| 2008/0140217 A1 | * | 6/2008 | Li et al. ...................... | 623/23.51 |
| 2009/0148601 A1 | * | 6/2009 | Ruberti et al. ................ | 427/256 |
| 2009/0269586 A1 | * | 10/2009 | Parma et al. ................ | 428/411.1 |
| 2010/0272782 A1 | * | 10/2010 | Owens et al. ................. | 424/443 |

FOREIGN PATENT DOCUMENTS

WO    WO 2006003442 A2 *  1/2006
WO    WO 2007060459 A2 *  5/2007

OTHER PUBLICATIONS

Miller et al., "Preparation and Characterization of the Different Types of Collagen", Methods in Enzymology, vol. 82, pp. 33-64, 1982.
Schofield et al., "The Isolation and Amino-Acid and Carbohydrate Composition of Polymeric Collagens Prepared from Various Human Tissues", Biochemical Journal, vol. 124, No. 3, pp. 467-473, 1971.
Spichtin et al, "Calcium as stabilizing factor of the collagen macromolecule", Experientia, Birkaueser Verlag., vol. 25, No. 1, pp. 9-13, 1969.

* cited by examiner

*Primary Examiner* — Karen Cochrane Carlson
*Assistant Examiner* — Samuel Liu
(74) *Attorney, Agent, or Firm* — Nixon Peabody LLP; David S. Resnick; Leena H. Karttunen Contarino

(57) ABSTRACT

This invention relates to the production of biomaterials from polymeric collagen (PC) and its seeding with cells and other components of biomaterials. Polymeric collagen is isolated from tissue, suspended in an acidic solution, and then neutralized at low temperature. The neutralized suspension is then seeded with biomaterial components, such as cells, and the polymeric collagen aggregated to form a biomaterial comprising the biomaterial components. Polymeric collagen biomaterials produced as described herein may therefore be useful in a range of tissue engineering applications.

13 Claims, 6 Drawing Sheets

Note this collagen gel is random fibril alignment and non cross-linked- so mechanically is not tough (a)

(b)

(c)

POLYMERIC COLLAGEN BIOMATERIALS

CROSS REFERENCE TO RELATED APPLICATIONS

This application is a 35 U.S.C. §371 National Phase Entry Application of International Application No. PCT/GB2010/001361, filed Jul. 16, 2010, which designated the United States, and which claims benefit under 35 U.S.C. §119(a) of the GB application No. 0912399.3, filed on Jul. 16, 2009.

This invention relates to the production of polymeric collagen biomaterials.

Collagen is the major structural protein of human and animal connective tissues. It is widely accepted as a safe and natural biomaterial for the manufacture of a broad range of collagen-based food, cosmetic and medical products.

Collagen is commonly used in the construction of engineered biomimetic collagenous tissues for therapeutic applications. These biomimetic tissues are generally made from collagen gels produced from native collagen.

Native collagen is harvested directly from animal tissues and is strong and highly organised, but does not contain cells. For example, although small intestinal submucosa (SIS) has been widely used as a biomaterial (S. F. Badylak et al. *J. Biomed. Mater. Res.* 1995 29 977), cells can only be seeded onto the material and cannot be inserted into the collagen structure without destroying its micro-nano-architecture. In addition, native collagen tissue cannot be easily engineered or tailored to specific needs.

Collagen gels are fabricated from soluble monomeric collagen and may be readily seeded with cells. However, collagen gels rely on the fibrillogenesis (gelling) of collagen monomer around the cells and are themselves weak and relatively poorly organised.

Given the deficiencies of both natural collagen material and collagen gels for tissue engineering, there is a need for biomaterials which are cross-linked, tough and organised, but which can have cells seeded interstitially where and when required, to allow the biomaterials to be engineered to specific needs.

The major fraction of most collagen tissue is polymeric collagen (PC), which is cross-linked (native) and has large diameter fibrils (i.e. tough/aligned). Polymeric collagen may be purified from native collagen tissue by swelling the polymer at low pH into a clear solution/suspension, and then re-condensing/re-aggregating the collagen fibres by neutralisation (Steven F. S. (1967) Biochim. Biphys. Acta 140, 522-528; Schofield, J. D. et al (1971) Biochem. J. 124, 467-473; Steven, F. S. et al (1969) Gut 10, 484-487).

However, although polymeric collagen was first described over 40 years ago, pure polymeric collagen has not been used extensively for tissue engineering applications because of the apparent difficulty of seeding pure polymeric collagen with viable cells and other components of biomaterials.

The present inventors have developed a process that allows polymeric collagen (PC) to be purified and seeded with cells and other components of biomaterials. Biomaterials produced by this process are mechanically strong compared with monomeric collagen gel-based biomaterials but can be engineered according to the specific application, unlike preparations of whole tissues. Polymeric collagen biomaterials produced as described herein may therefore be useful in a range of tissue engineering applications.

An aspect of the invention provides a method of producing a polymeric collagen biomaterial comprising;
(i) depleting calcium from a sample of collagen tissue,
(ii) dispersing the calcium depleted tissue sample in an acid solution to produce a tissue suspension,
(iii) neutralising the tissue suspension and aggregating the polymeric collagen therein,
(iv) removing aggregated polymeric collagen from the neutralised tissue suspension,
(v) dispersing the aggregated polymeric collagen in an acidic solution to produce a polymeric collagen suspension,
(vi) neutralising the polymeric collagen suspension and aggregating the polymeric collagen therein,
(vii) removing aggregated polymeric collagen from the neutralised suspension,
(viii) optionally performing one or more repetitions of steps (v) to (vii),
(ix) dispersing the aggregated polymeric collagen in an acidic solution to produce a purified polymeric collagen suspension,
(x) neutralising the purified polymeric collagen suspension at low temperature without aggregating the polymeric collagen therein,
(xi) mixing one or more biomaterial components into the neutralised suspension, and;
(xii) aggregating the polymeric collagen in the suspension to form a biomaterial.

Neutralisation of the purified polymeric collagen suspension at low temperature in step (x) and slows the aggregation of the polymeric collagen. Low temperature may be from 0 to 10° C., preferably 0 to 5° C., typically about 4° C. Preferably, the suspension is not agitated or is subjected to an amount of agitation which is insufficient to induce aggregation. This allows the biomaterial components, such as cells, to be admixed into the polymeric collagen suspension in the liquid phase. After the biomaterial components are admixed into the liquid suspension, the purified polymeric collagen aggregates to form a solid biomaterial which incorporates the biomaterial components.

Optionally, the polymeric collagen may be incubated a prolonged period following final aggregation in step (xii), for example for 1 or more, 2 or more or 3 or more hours, to allow the collagen to condense into a tightly packed structure.

Following in step (xii) and optional further condensation, the polymeric collagen biomaterial may be in an amorphous, mat or sheet form. The biomaterial may then be further processed and/or used as appropriate, for example for the production of a tissue equivalent implant.

Collagen tissue is tissue obtained from a natural source which contains collagen. Preferably, the collagen tissue is mammalian or avian collagen tissue. Examples of collagen containing tissues include bone, skin, tendon and ligament. Preferably, the collagen tissue is ligament or tendon, which has been found to have low levels of contaminants. In some preferred embodiments, tendon from a large flightless bird, such as an ostrich, emu or cassowary, may be employed.

The collagen tissue sample may be selected to produce the level of final product cross-linking (i.e. polymerisation) which is required for the desired application and process.

To facilitate swelling and dispersal of the tissue sample at low pH, it is preferred that the collagen tissue sample contains little or no inter-fibrillar covalent cross-linkages (i.e. covalent cross-linkages are substantially all intra-fibrillar). Preferred collagen samples may be obtained from immature animals, such as infants or juveniles, since collagen in mature adult tissue commonly contains extensive inter-fibrillar cross-linking.

Collagen tissue contains two types of collagen. Monomeric collagen, which is acid soluble and forms short chains, represents up to 20% of the total collagen in collagen tissues. Polymeric collagen represents 80% or more of the total collagen in collagen tissues. Polymeric collagen is insoluble and comprises aligned strands of collagen fibres which are covalently cross-linked and organised into large diameter fibrils. Collagen fibrils may be of any native fibril-forming collagen type, including collagen types I, II, III, V, VI, VII, IX and XI (II, IX, XI in cartilage tissues only) and combinations of these (e.g. I, III V or II, IX, XI etc). More preferably, the collagen fibrils are of collagen type I, II or III.

For example, the fibrils may be collagen type I fibrils or combinations of types I, III and V or types II, IX and XI.

Polymeric collagen is distinct from monomeric collagen, which forms weak gels with random fibril organisation. Polymeric collagen is also distinct from collagen sponges, which are random porous structures derived from extensively pre-polymerised fibres (I. V. Yannas et al *Science* (1982) 215, 174) and denatured collagen gels, such as gelatin.

Conveniently, a sample of collagen tissue for use in the present methods is fragmentated into small particles, preferably a powder. This increases the surface area of the sample and facilitates permeation of treatment agents such as chelators and acids.

The collagen tissue sample may be processed into powder before use. Any convenient method may be employed, including liquid nitrogen fracture, vibrational fragmentation or industrial shredding or slicing. For example, a sample of collagen tissue may be fragmented, for example by cutting into small sections or pieces, frozen, preferably in liquid nitrogen, and then pulverised, for example in a hammer mill, to form a powder.

In native collagen tissue, non-collagen proteins, such as proteoglycans, are bound to collagen fibres by calcium bridges. Calcium depletion removes calcium from the collagen sample and eliminates these calcium bridges. Once these calcium bridges are broken, the collagen polymer fibrils are released from non-collagen proteins and may be purified by cycles of acid swelling and collapse as described below.

Calcium may be depleted from the collagen tissue sample by any suitable technique.

For example, calcium may be depleted by soaking the collagen tissue sample in $Ca^{2+}$ free aqueous solution. Suitable $Ca^{2+}$ free aqueous solutions include citrate buffer or water (Veis et al 1970 Biochim Biophys Acta. 1970 Jan. 20; 200(1): 97-112). Alternatively, calcium may be depleted by treating the collagen tissue sample with alpha amylase (Steven F. S. Ann Rheum Dis. 1964 July; 23:300-1).

The sample may be immersed in a $Ca^{2+}$ free aqueous solution until maximal swelling has occurred. This may be visually determined. For example, the sample may be treated for 24 or more, 48 or more, or 72 or more hours, preferably at low temperature (e.g. 0 to 10° C.) Typically, the sample may be incubated in the solution for 5, 10 or 15 days.

In some embodiments, $Ca^{2+}$ may be depleted by treating the collagen tissue sample with a $Ca^{2+}$ chelator. The volume and concentration of the $Ca^{2+}$ chelator are preferably in excess of the treated tissue to facilitate rapid and complete $Ca^{2+}$ depletion with maximal swelling of the polymeric collagen. For example, the collagen tissue sample may be immersed in a solution comprising a $Ca^{2+}$ chelator for 12 or more, 24 or more or 48 or more hours, preferably at low temperature (e.g. 0 to 5° C.). Typically, the sample may be incubated in the solution for 48-72 hours.

Suitable non-toxic $Ca^{2+}$ chelators are well-known in the art and include EDTA and EGTA. For example, the sample may be immersed in 1% to 10% (w/v) EDTA, typically 4% (w/v) EDTA.

The collagen tissue sample is preferably treated with the $Ca^{2+}$ chelator at a neutral pH, for example pH 7 to pH 8. Typically, the solution is at pH 7.4. Suitable buffers to adjust and maintain pH are well-known in the art. In some preferred embodiments, the tissue sample may be suspended in 4% (w/v) EDTA at pH 7.4 for 48-72 hours at about 4° C.

Following calcium depletion, the collagen tissue sample may be washed. Suitable wash solutions include aqueous solutions, such as water or buffer.

The calcium depleted collagen tissue sample is then exposed to a low pH by treatment with acid. For example, the sample may be immersed in an acidic solution having a pH of 1 to 4 with optional mixing or stirring to produce an acidic suspension of the sample. At low pH, carboxyl groups within the collagen are protonated. This disrupts non-covalent bonds between collagen fibrils and in the absence of non-covalent binding, the collagen fibrils disperse and the sample swells.

Suitable acids include organic acids such as acetic acid and citric acid, and mineral acids, such as HCl.

The acid strength and length of acid treatment are sufficient to swell the collagen tissue sample without hydrolysing the polymeric collagen. For example, the collagen tissue sample may be dispersed in a 0.05M to 2M acetic acid, preferably 0.1M to 0.5M, for example about 0.2M acetic acid. In some embodiments, the collagen tissue sample may be treated with acid at low temperature (e.g. 0 to 10° C.). This helps to reduce microorganism growth and slows down gel formation. For example, the collagen tissue sample may be dispersed in 0.2M acetic acid at 4° C.

The calcium depleted collagen tissue sample may be treated with acid until it is fully dissolved and/or dispersed, for example for 1 hours or more, 6 hours or more, 12 hours or more, 18 hours or more or 24 hours or more.

The dispersal of the calcium depleted sample in the acid may be readily determined by visual observation.

The acid suspension of collagen tissue is then neutralised to produce a neutralised suspension. Neutralisation causes non-covalent bonds between collagen fibrils to reform through charge condensation and increased proximity of short range charge groups on adjacent chains. The reformation of these inter-fibrillar bonds causes the polymeric collagen to aggregate.

The acid suspension may be neutralised using any convenient technique. Typically, the pH of the acid suspension is increased to neutral pH (pH 7 to 8) by titration with a base solution. Suitable base solutions are well-known in the art and include NaOH at 0.05M to 5 M. Preferably, the base solution is distributed uniformly within the suspension to achieve uniform gelling.

During or after neutralisation, the polymeric collagen in the suspension is aggregated. Any suitable technique may be employed.

The polymeric collagen may be aggregated by incubating the neutralised solution until aggregation occurs.

The neutralised solution may be left static (i.e. without stirring or other agitation) during the incubation.

Alternatively the neutralised solution may be agitated to promote aggregation of the solution. The neutralised solution may be agitated by any convenient method, for example the solution may be stirred, shaken, centrifuged or filtered. Agitation increases the proximity and alignment of the collagen fibrils in the solution and therefore promotes the reformation of short range non-covalent bonds between the fibrils.

The neutralised suspension may be static incubated or subjected to agitation to induce aggregation at any suitable temperature (e.g. 0° C. to 40° C.)

Aggregation is shown herein to be delayed by incubation at low temperature. For example, the neutralised solution may be incubated at low temperature (e.g. 0 to 10° C.) to delay aggregation. The suspension may be subjected to static incubation at low temperature for 30 mins or more, 1 hour or more, 2 or more, or 3 or more hours to allow aggregation of the polymeric collagen or subjected to agitation for 5 mins or more, 10 mins or more or 15 mins or more.

Neutralisation and aggregation at low temperature (e.g. 0 to 10° C.) may be helpful in reducing contamination from monomeric collagen. Although monomeric collagen is unlikely gel or aggregate at the low concentrations present in the neutralised suspension even at room temperature, neutralisation at low temperature ensures that no monomeric collagen aggregates or gels, so only polymeric collagen aggregates and is extracted from the neutralised suspension.

Aggregation is shown herein to be accelerated by incubation at increased temperature. For example, the neutralised solution may be incubated at high temperature (e.g. 25 to 40° C.) to accelerate aggregation. This may be useful in accelerating the trapping of cells within the biomaterial.

After aggregation, the polymeric collagen aggregates may be removed whilst monomeric collagen, non-collagenous proteins and other contaminants remain in solution.

Any convenient technique may be used to remove or separate aggregated polymeric collagen from the solution. For example, the aggregated polymeric collagen may be manually lifted out of the suspension e.g. with a stirring rod or sieving of monomeric collagen solution out.

After removal from the neutralised suspension, the aggregated polymeric collagen may then optionally be subjected to further rounds of acid treatment, neutralisation and separation as described above. This progressively purifies the polymeric collagen from soluble monomeric collagen and other contaminants which may be present in the collagen tissue sample. The polymeric collagen aggregate may, for example, undergo 1, 2, 3, 4, 5 or 6 or more cycles of acid treatment, neutralisation and separation before reaching the desired level of purity.

Repetitions of steps (v) to (vii) purify the polymer from monomeric collagen and soluble non-collagenous proteins such as proteoglycans, serum proteins, cytoplasmic and protease proteins within the sample of collagen tissue (Grant et al Biochem J. 1968 July; 108(4):587-91).

When the polymeric collagen has undergone sufficient purification, it is subjected to a final acid treatment and neutralisation. The final neutralisation is carried out at low temperature with insufficient agitation to induce aggregation. For example, the final neutralisation may be carried out in the absence of agitation (e.g. stirring) or with minimal agitation to delay the onset of aggregation of the polymeric collagen. For example, the final neutralisation may be performed at 0 to 10° C., preferably 0 to 5° C. and typically about 4° C.

At low temperature, in the absence of agitation-induced aggregation, the neutralised polymeric collagen remains in a liquid form for up to 30 min or more. One or more biomaterial components may then be added to the liquid polymeric collagen.

Biomaterial components may include mammalian cells, solid elements, biomatrix components and/or therapeutic agents. Biomaterial components, such as cells, may be added to the neutralised polymeric collagen by pipette seeding, followed by gentle mixing into the liquid suspension without inducing shear aggregation of the polymeric collagen.

Mammalian cells may include muscle cells to provide contractile structures, vascular and/or neural cells to provide conductive elements, metabolically active secretory cells, such as liver cells, hormone synthesising cells, sebaceous cells, pancreatic islet cells or adrenal cortex cells to provide secretory structures, fibroblasts, such as dermal fibroblasts, skin keratinocytes, melanocytes (and combination layers of the two), Schwann cells for nerve implants, smooth muscle cells and endothelial cells for vessel structures, urothelial and smooth muscle cells for bladder/urethra structures, osteocytes, chondrocytes, and tendon cells for bone and tendon structures and stem cells, such as corneal (limbal) stem cells, skin epidermal stem cells, gut (intestinal) stem cells, orogenital stem cells, bronchial and other epithelial stem cells, bone marrow stem cells, growth plate stem cells.

In some preferred embodiments, the cells may be dermal fibroblasts, keratinocytes, melanocytes, stem cells or chondroytes.

Cells may be distributed interstitially within the biomaterial in any arrangement. For example, the cells may be distributed homogeneously throughout the biomaterial or distributed in defined zones, regions or layers within the biomaterial.

Incorporation of viable cells into the liquid suspension of polymeric collagen is preferably performed under suitable conditions of temperature, neutral pH, ionic strength and sheer to maintain viability.

The initial cell density in the polymeric collagen suspension may be from about $1 \times 10^4$ to $1 \times 10^7$ cells per ml, more preferably from about $5 \times 10^5$ to $1 \times 10^6$ cells per ml.

Solid elements may include tubes, such as carbon nanotubes; particles such as metal or hard tissue particles, nanoparticles, magnetic particles and imaging particles, such as radio-opaque, ultrasound reflective or fluorescent particles; fibres, such as capillary filaments; and vesicles such as lipid/phosphor lipid vesicles, liposomes and slow-release drug vesicles.

Biomatrix components may include hyaluronic acid, elastin, fibrin, fibronectin, silk or other nano-micro fibrous materials, and collagen.

Suitable hard tissue particles may be approximately 100-500 microns in diameter and may be of any solid material or mineral, for example porous ceramic, tricalcium phosphate, silicone, glass, bioglass, phosphate glass, hydroxapatite, or bone mineral preparations (from native bone removal of organic phase).

Hard tissue particles may be incorporated into the biomaterial along with osteoblasts or chondrocytes, to produce an artificial bone or calcified cartilage substitute tissue. The ratio of particles to biomaterial and cells will depend on the particle size and the tissue properties required (e.g. dense or loose packed hard tissue).

In some embodiments, hard tissue particles as described herein may be incorporated at the ends of a linear construct produced from the biomaterial, to facilitate attachment of the construct in vivo, for example by screwing directly into bone.

Capillary filaments may be insoluble or soluble fibres of a rigid, solid polymer. Suitable filaments are preferably less than about 100 μm in diameter.

Soluble filaments inserted within the biomaterial may dissolve to form capillary channels within the biomaterial. These capillary channels within the biomaterial may be useful for example, for one or more of: perfusion, drug and/or gene and/or media delivery into the scaffold; and anastomosis with a recipient's circulation. Suitable soluble filaments may be made from soluble phosphate glass, polycapryolacetone, polyacetate, polyglycolic acid, silks, polysaccharides, or fused or crystallised salts.

Insoluble filaments may be useful for delivering optical therapies, optical monitoring, signal transmission and/or strain detection. Suitable insoluble filaments may be made from glass.

In some preferred embodiments, the biomaterial component may be hydroxyapatite, hyaluronic acid, elastin, and/or phosphate-based glass.

Biomaterial components may include therapeutic agents. Polymeric collagen biomaterials incorporating therapeutic agents may be useful as capsules, depots or implants which release the therapeutic agent in situ in a patient or may themselves incorporate capsules, liposomes, vesicles or depots containing therapeutic agents.

Therapeutic agents may include small organic molecules, proteins, such as antibody molecules, hormones, cytokines, chemokines, growth factors, viruses, nucleic acid molecules, such as aptamers or antisense or sense suppression molecules, vectors, antibiotics, or micro-organisms.

After mixing the biomaterial components into the neutralised polymeric collagen suspension, the polymeric collagen may be allowed to solidify to form a solid biomaterial which incorporates the biomaterial components.

For example, the neutralised polymeric collagen suspension may be kept at low temperature e.g. (0 to 4° C.) without stirring or agitation and allowed to solidify. This may, for example, take 60 to 120 mins. Alternatively, solidification may be accelerated (for example, to less than 60 min) by warming the suspension, for example up to 40° C.

After the incorporation of biomaterial components, the neutralised polymeric collagen suspension may be subjected to shear stress. In addition to promoting aggregation, this may be useful in aligning collagen fibrils and cells if present, parallel to the shear during solidification. For example, shear stress may be applied to the polymeric collagen during the initial stages of solidification before it finally sets into its dense fibrous form. Shear stress may be applied, for example, by mechanical stirring, to align the cells in the direction of rotation. The resultant biomaterial comprises cross-linked aligned fibres, and optionally aligned cells. This biomaterial is mechanically strong and possesses tissue-like properties.

As the polymeric collagen in the neutralised suspension aggregates and solidifies, the collagen fibrils come together and trap biomaterial components seeded into the liquid suspension.

After solidification, the polymeric collagen biomaterial may be stored, used for tissue engineering applications or processed further.

To reduce and/or prevent cell death or damage, a biomaterial comprising viable cells may be stored under conditions which maintain viability but which do not support cell growth, until ready for use. For example, the biomaterial may be stored at low temperature e.g. 0 to 10° C. or frozen (<0° C.) in the presence of a cryoprotectant. The biomaterial can be stored in cell culture medium at 37° C. for short periods of time. In some embodiments, the biomaterial is not subjected to drying or desiccation, for example heat, airflow or vacuum drying, as dehydration kills cells and damages biomaterial structure.

Other aspects of the invention provide a polymeric collagen biomaterial obtainable or obtained by a method described above and a biomaterial comprising polymeric collagen having heterologous biomaterial components, such as viable mammalian cells, incorporated therein.

Heterologous biomaterial components are components which have been artificially introduced into the polymeric collagen and are not found in polymeric collagen purified from collagen tissues using conventional techniques (see for example Steven, F. S. and Jackson, D. S. (1967), Biochem. J. 104, 534).

Polymeric collagen biomaterials may be useful in cell therapy, pharmaceutical development, cell culture, orthopaedics, dermatology and wound healing.

Polymeric collagen biomaterials may be useful as 3-dimensional model tissues for toxicological, pharmacological and pathogen screening as well as other research purposes. Polymeric collagen biomaterials may also be useful as coatings, fillers and for conventional (e.g. metal or plastic) prosthetic implants or as capsules, depots or implants for controlled in situ drug release.

Biomaterials may also be useful in the production of tissue equivalent implants.

A tissue equivalent implant is a material for implantation into an individual to repair or replace endogenous tissue, which, for example, may be damaged or diseased. Examples of tissues which may be repaired or replaced by tissue equivalent implants include nerves, tendons, ligaments, cartilage, skin, fascia, bone, urogenital elements, liver, cardiopulmonary tissues, kidney, ocular tissues, such as the cornea, blood vessels, intestine, and glands.

Diseased or damaged tissue may for example result from arthritides, neuro-muscle injury/degeneration, musculo-tendenous failure and age-degeneration, poor regeneration after trauma (e.g. burns), tissue necrosis or surgical resection (e.g. tumour surgery).

To produce a tissue equivalent implant, the polymeric collagen biomaterial may undergo additional processing, e.g. plastic compaction, uniaxial fluid shear, tissue culture, moulding and/or shaping.

For example, after production as described above, the polymeric collagen biomaterial may be subjected to plastic compaction. Plastic compaction may be symmetrical or asymmetrical and is described in more detail in WO2006/003442; WO2007/060459; and Brown, R. A. et al (2005). Adv. Funct. Mater. 15, 1762-1770

Uniaxial fluid shear may be applied to the polymeric collagen biomaterial to help align fibrils as they aggregate and reduce the water content of the biomaterial to required levels.

After production, the polymeric collagen biomaterial may be subjected to tissue culture to allow resident cells in the biomaterial to deposit minor components and remodel the collagen material The biomaterial may be shaped, cut or moulded into any convenient implant form, for example, a patch, block, tube, tape, strip, ring, sphere, toroid, capillary, roll, sheet or thread to produce a tissue equivalent implant. The final shape of the implant will depend on the particular context in which it is to be used. In some embodiments, the implant may have a pliable form which is suitable for further shaping.

In some embodiments, a sheet or strip of polymeric collagen biomaterial may be rolled up or folded to form a multi-layered construct e.g. a roll. This multi-layered construct may be used directly as a tissue equivalent implant or may be further cut, shaped or moulded as required. In some embodiments, the multi-layered construct may be plastically compacted to adhere multiple layers together, achieve the desired dimensions, increase cell density or to improve other properties.

Other aspects of the invention relate to polymeric collagen biomaterial as described herein for use as a tissue equivalent implant and the use of a polymeric collagen biomaterial as described herein in the manufacture of a medicament for use as a tissue equivalent implant.

A tissue equivalent implant may be suitable for a therapeutic application described above.

Another aspect of the invention provides a tissue equivalent implant comprising or consisting of a polymeric collagen biomaterial produced or producible by a method described herein.

Another aspect of the invention provides a method of treatment of a damaged or defective tissue in an individual comprising;
fixing a tissue equivalent implant as described herein to said tissue to repair and/or replace said tissue.

The implant may be fixed by any convenient technique. For example, it may be sutured or glued in place.

Implants produced from the polymeric collagen biomaterials described herein will take sutures and can be sutured surgically into body sites even when under muscle load.

Other aspects of the invention relate to the production and storage of monomeric collagen.

The neutralized monomeric collagen solutions which remain after removal of aggregated polymeric collagen as described above are highly stable and may be stored in liquid form at low temperature for long time periods (e.g. two weeks or more).

These neutralized solutions may therefore be useful for transporting and handling monomeric collagen, and avoiding the batch-to-batch variability which arises from the neutralisation of small batches of acidic collagen solution by the end-user.

A method of producing monomeric collagen may comprise;
(i) treating a sample of collagen tissue with a calcium chelator,
(ii) dispersing the treated sample of collagen tissue in acid to produce a tissue suspension,
(iii) neutralising the tissue suspension with stirring at low temperature to aggregate polymeric collagen in said suspension,
(iv) removing the aggregated polymeric collagen from the suspension to produce a solution of monomeric collagen, and;
(v) storing the monomeric collagen solution.

The monomeric collagen solution may be stored and transported at low temperature e.g. less than 5° C. This prevents endothermic gelling of the neutralised soluble collagen.

In some embodiments, the neutralised collagen solution may be frozen for storage and transport e.g. at less than 0° C., for example at –5° C. to –70° C., typically about –20° C.

The monomeric collagen solution may be seeded with mammalian cells, for example autologous or allogeneic cells (e.g. keratinocytes or melanocytes).

In some embodiments, monomeric collagen solution seeded with mammalian cells may comprise a cryoprotectant, such as DMSO, ethylene glycol, glycerol, propylene glycol, sucrose or trehalose.

The cryoprotectant protects cells when the solution is frozen and maintains their viability until thawing. When the monomeric collagen solution is thawed and exposed to room temperature e.g. in contact with body, it solidifies.

In use, the neutralised solution of monomeric collagen may be positioned in a suitable environment, such as a cast or mould, and warmed, for example to room temperature or 37° C., to initiate solidification. The solution then solidifies in the environment.

Other aspects of the invention relate to the use of monomeric collagen and aggregated polymeric collagen in cosmetic formulations.

A cosmetic formulation may comprise a monomeric collagen solution as described above. The formulation may be stored at low temperature In use, the formulation in its low temperature liquid form may be contacted with the body. Following contact with the body, the formulation warms up and the neutralised collagen solidifies to form a gel.

Neutralized aggregated polymeric collagen may be added to the monomeric collagen solution to produce a cosmetic formulation which comprises a mixture of monomeric collagen solution and aggregated polymeric collagen particles. For example, a formulation may comprise 0.01% to 99% polymeric collagen.

As described above, the formulation may be stored as a liquid at low temperature. In use, the composition warms up and solidifies to form a gel containing both the monomeric and polymeric collagen fractions.

A method of cosmetic treatment may comprise;
contacting a cosmetic formulation comprising monomeric collagen solution with the body of an individual, and;
allowing the formulation to solidify.

The cosmetic formulation may further comprise neutralised aggregated polymeric collagen, as described above.

The monomeric collagen solution and/or aggregated polymeric collagen may be acellular or may be seeded with cells as described herein.

Cosmetic formulations may further comprise other biomolecules, such as hyaluronic acid and elastin.

In some embodiments, cosmetic formulations may be applied to the skin (e.g. in the form of liquid, absorbable gel, or mask) to improve moisture content, aid regeneration, fill pores and reduce wrinkles (anti-aging effect) or the hair (e.g. in the form of a shampoo, hair serum or gel).

In other embodiments, cosmetic formulations may be injected to fill an internal cavity to alter the aesthetic appearance of the body, for example the formulation may be used as a lip filler or breast implant.

Other aspects of the invention relate to the use of polymeric collagen, monomeric collagen or mixtures thereof as therapeutic formulations, for example as an injectable polymer for regenerative applications.

A therapeutic formulation may comprise a monomeric collagen solution as described above. The formulation may be stored at low temperature In use, the formulation in its low temperature liquid form may be contacted with the body. Following contact with the body, the formulation warms up and the neutralised collagen solidifies to form a gel.

Neutralized aggregated polymeric collagen may be added to the monomeric collagen solution to produce a therapeutic formulation which comprises a mixture of monomeric collagen solution and aggregated polymeric collagen particles. For example, a formulation may comprise 0.01% to 99% polymeric collagen.

As described above, the therapeutic formulation may be stored as a liquid at low temperature. In use, the composition warms up and solidifies to form a gel containing both the monomeric and polymeric collagen fractions.

A method of treatment may comprise;
contacting a therapeutic formulation comprising monomeric collagen solution with the body of an individual, and;
allowing the formulation to solidify.

The therapeutic formulation may further comprise neutralised aggregated polymeric collagen, as described above.

Therapeutic formulations may further comprise other biomolecules, such as hyaluronic acid and elastin, solid elements or therapeutic agents.

The therapeutic formulation may be acellular or may be seeded with mammalian cells as described herein. Formulations may be, for example seeded with autologous cells, such as fibroblasts, keratinocytes or melanocytes, and may be useful in the regeneration of the skin surface, for example in the treatment of aged or chemically/mechanically abraded skin, or example after micro-dermabration treatment.

Formulations may also be useful in forming skin patches for delivery of agents, cells or cell products to particular body sites.

Various further aspects and embodiments of the present invention will be apparent to those skilled in the art in view of the present disclosure.

All documents referred to above and below are incorporated herein by reference.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures described below.

EXPERIMENTS

Polymeric and monomeric collagens were extracted from ostrich tendon.

Ostrich tendon (~3 grams) was cut up finely, frozen in liquid nitrogen and disintegrated in a stainless steel hammer mill. The powdered form of tendon was incubated at 4° C. for 48-72 hours in 4% (w/v) EDTA (disodium salt) after adjusting pH to 7.4. Following washing process several times with distilled water, collagen was dispersed in 0.2M acetic acid at 4° C. with mixing/blending as required to disperse. This collagen suspension was neutralised and/whilst stirring vigorously at low temperature.

After removing polymeric collagen created around the stirring rod, it was kept 4° C. over night. The clear solution left at this stage was neutralised soluble collagen (mostly mono/oligomeric acid soluble collagen). This monomeric collagen solution was stored (for >2 weeks) at 4° C. for separate use for preparing conventional gels at 37° C.

The insoluble, aggregated collagen which was separated from the acid soluble (monomer) fraction was re-dispersed in 0.2 M acetic acid and repeatedly neutralised/re-aggregated then re-suspended in acetic acid, through as many cycles as needed to achieve the required protein purity (0-6 times).

In the last cycle, the neutralised, 4° C. polymeric collagen suspension was not immediately stirred. The solution was then mixed gently with cells and then allowed to gel.

As collagen fibrils are aligned during the stirring, shear stage cells can be aligned within the collagen gel without any further orientation process.

Polymeric collagen constructs were produced as described above.

Figure 1:
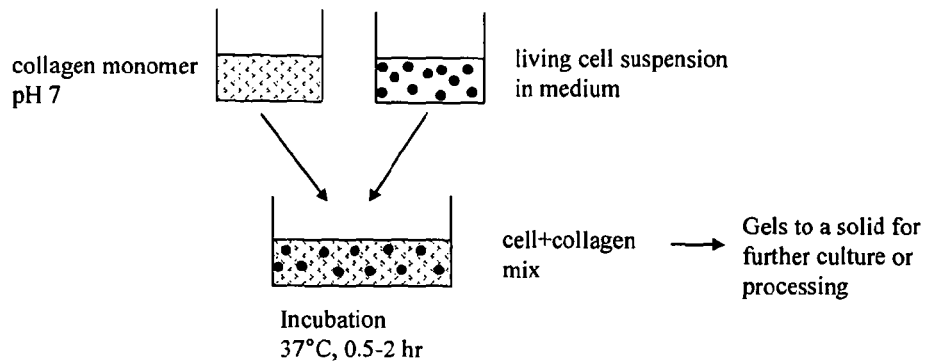
FIG. 1 shows prior art processes for incorporating cells into gels of monomeric collagen.
Figure 2:
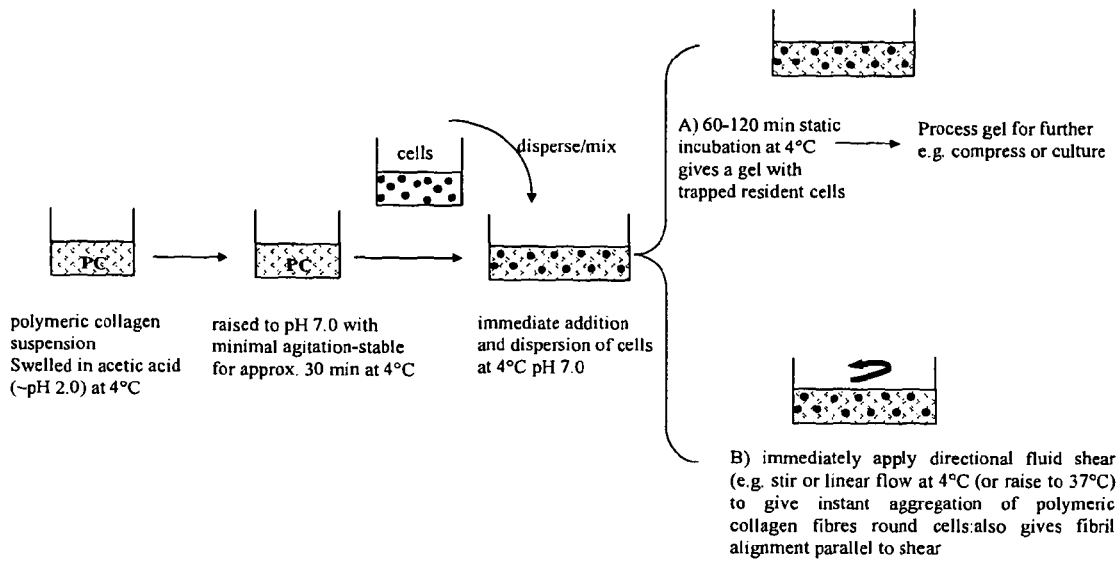
FIG. 2 shows the incorporation of cells into polymeric collagen to produce a cellularised polymeric collagen biomaterial.
Figure 3:
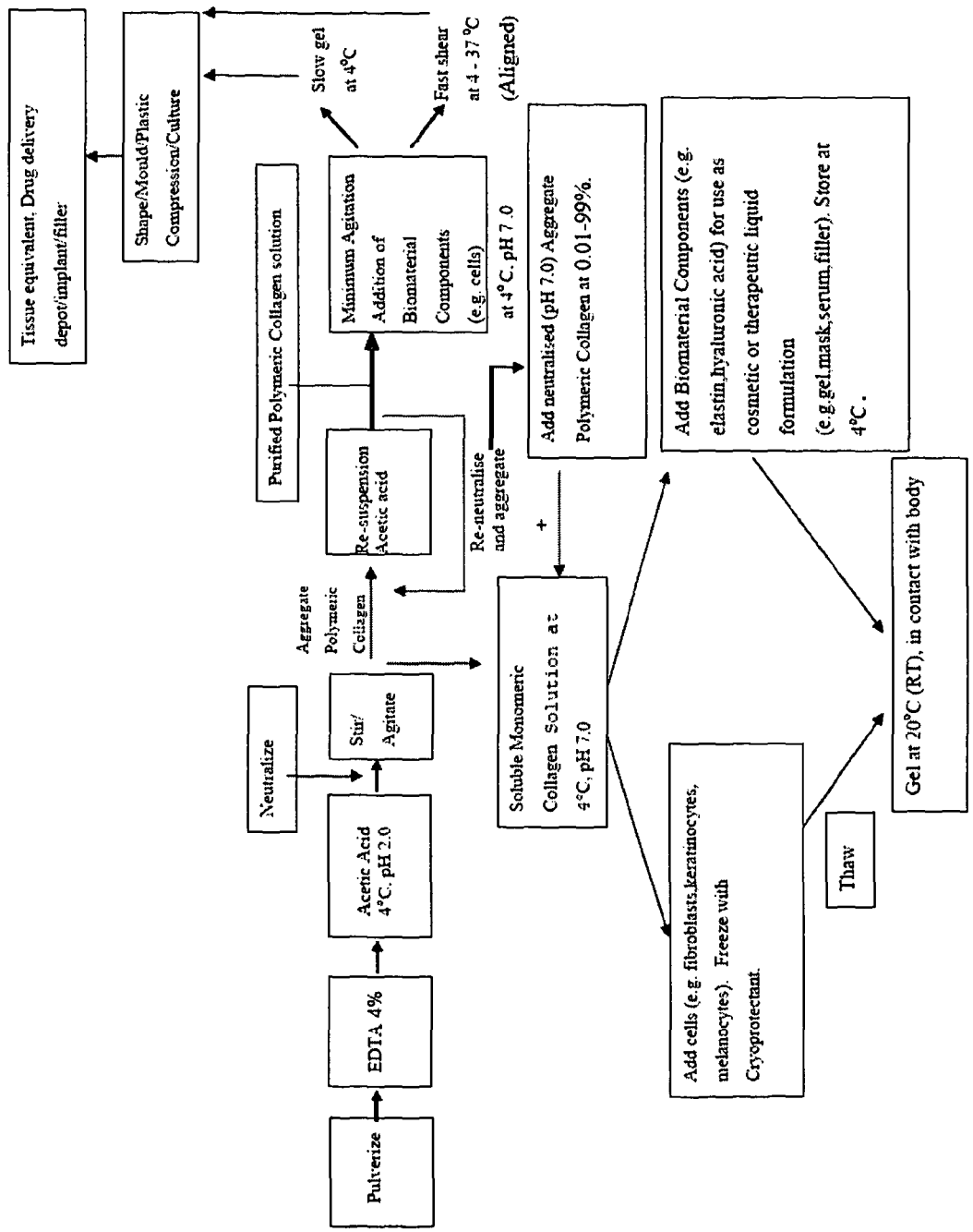
FIG. 3 shows a flow chart of the process for the production of biomaterials as described herein.
Figure 4:
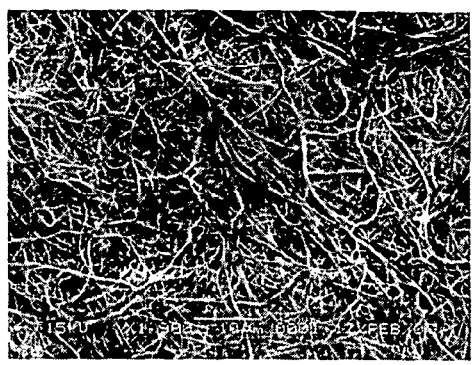
FIG. 4 shows scanning electron microscopy (SEM) images of polymeric collagen constructs, with strong embossing shown on the surface of the constructs.
Figure 4:
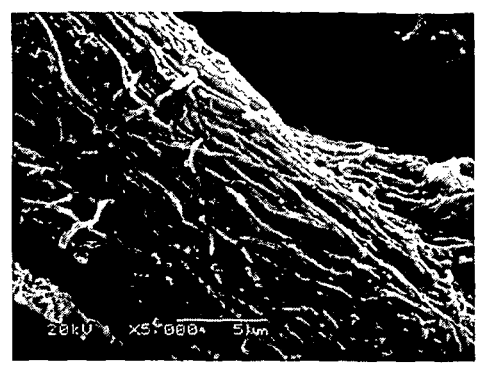
Figure 4:
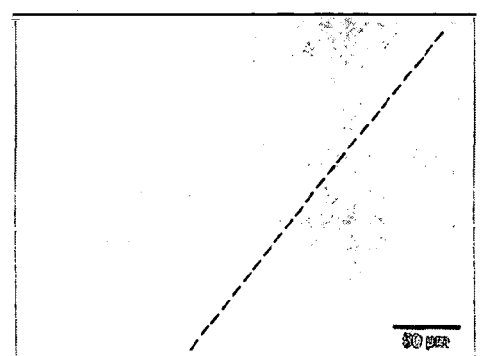

The structure of polymeric collagen constructs compared with control monomeric collagen constructs was investigated using scanning electron microscopy (SEM) and the results shown in FIG. 4. Monomeric collagen constructs were found to contain randomly oriented disorganised fibrils (FIG. 4a) whilst the fibrils of polymeric collagen constructs were aligned (FIGS. 4b and 4c).

Figure 5:
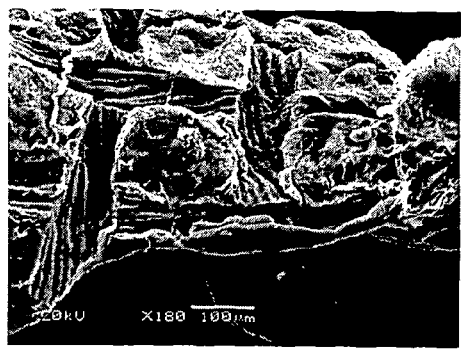
FIG. 5 shows scanning electron microscopy (SEM) images of (a) monomeric collagen-randomly oriented fibrils, disorganised (b) polymeric collagen-aligned fibrils and (c) polarized images of polymeric gelled collagen. The dashed line indicates direction of fibril alignment.
Figure 5:
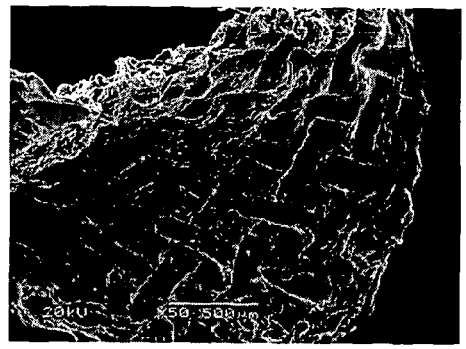

The polymeric collagen constructs were embossed with microstructure using a die. The results are shown in FIG. 5.

The anisotropy factor, AF (defined as ratio of backscattered light at perpendicular to parallel probe position at any given wavelength) of the polymeric collagen constructs compared with control monomeric collagen constructs was measured. The following results were obtained;

AF=1.72±0.19 (n=6) (Polymeric collagen, ostrich collagen)

AF=0.97±0.09 (n=6) (Monomeric collagen, rat tail collagen) Kostyuk and Brown, 2004, Biophysical Journal, 87; 648-655.

AF=2.72±0.38 (n=6) (Excised rabbit tendon) Morgan et al., 2006, Tissue Engineering, 12; 1821-1831.

Figure 6:
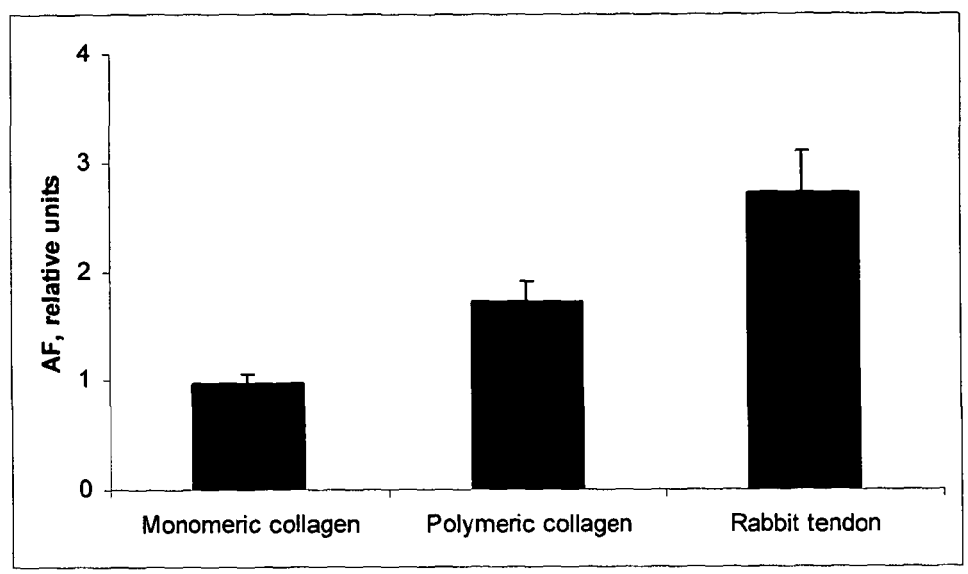
FIG. 6 shows the anisotropy factor, AF (defined as ratio of backscattered light at perpendicular to parallel probe position at any given wavelength) of monomeric and polymeric collagen constructs.

These results are illustrated graphically in FIG. 6.

The strength of monomeric and polymeric collagen constructs was tested by dynamic mechanical analysis (DMA). Constructs fabricated using polymeric collagen were found to be 2-3 times stronger than constructs of monomeric collagen.

Neutralised monomeric collagen solution was stored at 4° C. and −20° C. over 12 days (n=3) and periodically tested for gelling. Both samples gelled positively at all time points (Table 1).

Optical Computerised Tomography (OCT) is a non invasive technique which enables imaging of deep structures. An OCT microscope (Michelson-Diagnostics) with a resolution in the region of <5 μm through >1 mm depth of material was used. Three specimens were compared for their fine (cell free collagen) structure: i) Intact tendon; ii) orientated polymeric collagen sheet, prepared from ostrich tendon collagen (viewed parallel and perpendicular to preparation alignment; and iii) Gel formed from acid soluble rat-tail collagen and compacted (by plastic compression) to ~10% collagen content.

The compressed collagen gel appeared as a loose structure of completely random, homogeneous granules with no organisation and no identifiable structure. Material density was noticeably lower than the other two specimens.

The intact tendon was similar in overall density the PC Ostrich collagen, with modest signs of material alignment (at the resolution of the system), parallel with tendon axis, in much of the image and non-identifiable in others.

The polymeric collagen (viewed parallel with engineered alignment) appeared dense with cavity defects due to a prep artefact. These cavities and to a limited extent the dense collagen matrix material demonstrated modest signs of orientation, parallel with the specimen (i.e. confirming the orientation predicted to be produced by the preparation system). Alignment was not as pronounced as that of native tendon, but those signs of alignment which were visible in this parallel view were lost in the OCT image taken across (perpendicular to) the predicted alignment.

In conclusion, OCT analysis indicated that matrix packing of PC collagen was comparable to that of native tendon but much greater than compressed collagen gels (with approx. one half to one third the collagen density of tendon). The OCT technique was limited in its ability at this resolution, to image collagen fibre alignment, but there were indications of modest alignment in the predicted orientation in the polymeric collagen material, comparable though less marked than in native tendon.

Figure 7:
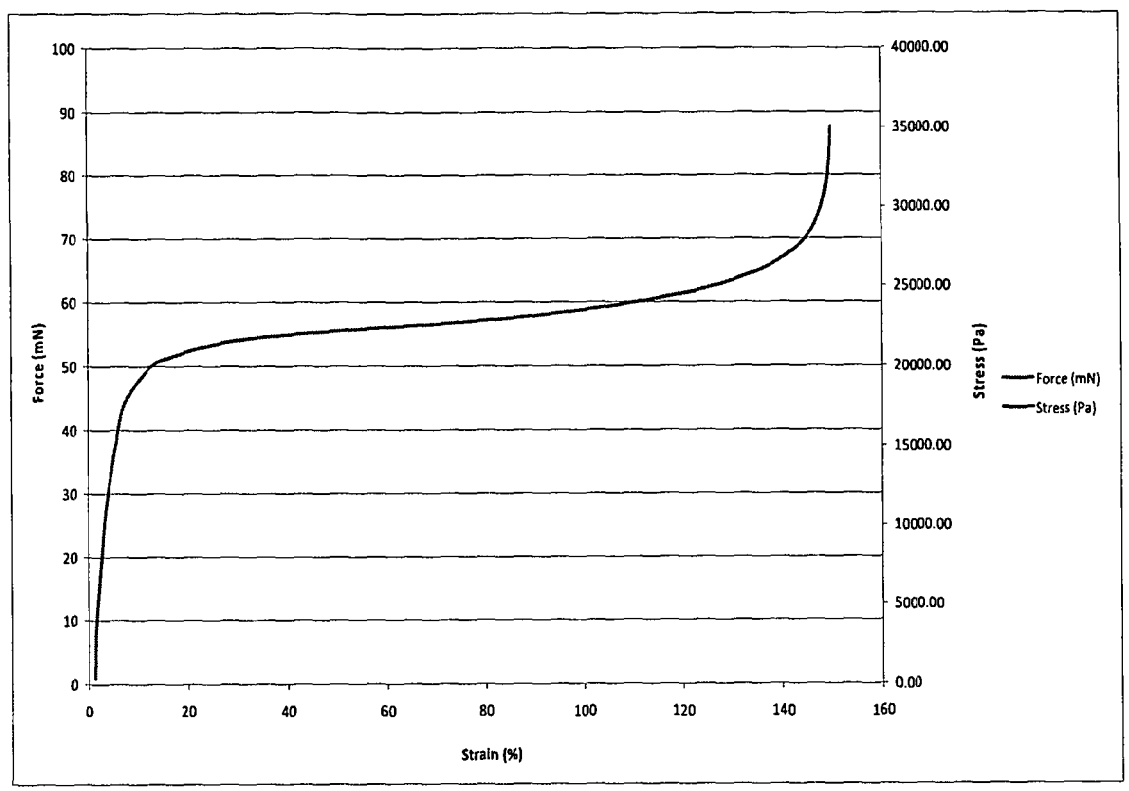
FIG. 7 shows a typical stress-strain curve for hydrated polymeric collagen gel from ostrich.

Stress-strain curves were recorded from DMA of collagen gels. An example of the behaviour of a transeversely orientated fibril ostrich collagen gel is shown in FIG. 7. Stress is derived from measurements of force and cross-sectional area of the material. Strain is the percentage deformation a material undergoes relative to its original length. The linear elastic region exhibits the force that the material may withstand to deform elastically, thus returning to its original length if applied force is removed. Within the elastic region, strain is directly related to stress; the slope of the line gives the Youngs modulus. A steep gradient denotes a stiff, brittle material; a shallow gradient indicates a more ductile material. Once the yield point is reached the material deforms plastically and will no longer return to its original length. The material continues to deform until reaching the break strength, equating to failure of the construct (Fratzl P J Struct Biol. 1998; 122(1-2):119-22.) FIG. 7 shows that hydrated collagen constructs are ductile in nature; the yield point is followed by a long plastic region before reaching failure.

Rat tail collagen sheets and all the subgroups of hydrated ostrich gels were assessed for variances in mean break strength on the application of 6000 mN at a rate of 200 mN min$^{-1}$. Table 2 shows the descriptive data for the collagen gel groups.

The viability of fibroblast cells (Dupuytren's fibroblasts) incorporated into polymeric collagen as described herein was assessed. Cell counts of viability were made in 2 different gels (polymeric monomeric mixture, static culture). Cells were counted in 3 different areas and 2 planes of the gels. Viability was found to be 96%+/−0.23 in the polymeric collagen. This shows that cells can be incorporated into polymeric collagen as it is fabricated and retain their viability.

TABLE 1

| Time | 4° C. | −20° C. |
|---|---|---|
| Day 0 | + | + |
| Day 1 | + | + |
| Day 2 | + | + |
| Day 5 | + | + |
| Day 12 | + | + |

TABLE 2

| Collagen Gels | Number of samples | Mean Break Strength N m$^{-2}$ | Standard Deviation | 95% Confidence Interval Lower Bound | 95% Confidence Interval Upper Bound |
|---|---|---|---|---|---|
| Rat Tail Sheet | 9 | 40743.33 | ±8550.79 | 34170.61 | 47316.05 |
| Ostrich Slow Gels | 17 | 50618.82 | ±21556.71 | 39535.38 | 61702.26 |
| Ostrich Batch A Hydrated | 7 | 21401.56 | ±8174.17 | 13841.71 | 28961.40 |
| Ostrich Batch B Hydrated | 8 | 40868.25 | ±15637.89 | 27794.64 | 53941.85 |
| Ostrich Long. Fibrils, 2 yrs | 7 | 104051.4 | ±39453.42 | 67563.09 | 140539.7 |
| Ostrich Trans. Fibrils, 2 yrs | 6 | 44551.67 | ±11576.95 | 32402.39 | 56700.93 |
| Ostrich Long. Fibrils, 6 mnths | 6 | 34820 | ±6864.39 | 27616.26 | 42023.73 |
| Ostrich Trans. Fibrils, 6 mnths | 7 | 22182.86 | ±1815.91 | 20503.42 | 23862.29 |

The invention claimed is:

1. A method of producing a polymeric collagen biomaterial Comprising:
   (i) depleting calcium from a sample of collagen tissue, optionally a sample of tendon or ligament from a bird or a mammal,
   (ii) dispersing the calcium depleted tissue sample in an acidic solution to produce a tissue suspension,
   (iii) neutralising the tissue suspension and aggregating the polymeric collagen therein,
   (iv) removing aggregated polymeric collagen from the neutralised tissue suspension,
   (v) dispersing the aggregated polymeric collagen in an acidic solution to produce a polymeric collagen suspension,
   (vi) neutralising the polymeric collagen suspension and aggregating the polymeric collagen therein,
   (vii) removing aggregated polymeric collagen from the neutralised suspension,
   (viii) performing one or more repetitions of steps (v) to (vii),
   (ix) dispersing the aggregated polymeric collagen in an acidic solution to produce a purified polymeric collagen suspension,
   (x) neutralising the purified polymeric collagen suspension at 0 to IO° C. without aggregation of the polymeric collagen therein,
   (xi) incorporating one or more biomaterial components into the neutralised suspension, and;
   (xii) aggregating the polymeric collagen in the suspension resulted from the step (xi) to form said polymeric collagen biomaterial.

2. The method according to claim 1 wherein the polymeric collagen is aggregated by agitation of the suspension in one or both of steps (iii) and (vi).

3. The method according to claim 1 wherein the collagen tissue sample is a powder, wherein the powder is prepared by a process comprising (i) fragmenting native collagen tissue wherein said fragmenting results in tissue fragments, (ii) freezing the tissue fragments and (iii) pulverising the frozen tissue fragments.

4. The method according to claim 1 wherein calcium is depleted from the collagen tissue sample in step (i) by suspending the sample in 4% (w/v) EDTA at pH 7 to 8 for 24 hours or more at low temperature; or wherein the calcium depleted tissue sample resulted from step (ii) is dispersed in the acidic solution ) at low temperature, optionally 0.2M acetic acid at 0 to 10° C., to produce the tissue suspension; or, wherein the tissue suspension in step (iii) is neutralised at low temperature.

5. The method according to claim 1 wherein steps v) and vi) are performed at low temperature.

6. The method according to claim 1 wherein steps (v) to (vii) are repeated up to 6 times.

7. The method according to claim 1 wherein the purified polymeric collagen suspension is neutralised without substantial agitation in step (x) to prevent aggregation of the polymeric collagen.

8. The method according to claim 1 wherein the biomaterial components comprise one or more of viable mammalian cells, solid elements and therapeutic agents.

9. The method according to claim 1 wherein the polymeric collagen is aggregated after incorporation of the biomaterial components by incubating at 0 to 10° C., or 0 to 5° C. without stirring or agitation.

10. The method according to claim 1 wherein, after incorporation of the biomaterial components, shear stress is applied to the polymeric collagen comprising collagen fibers during aggregation in step (xii) to align said collagen fibrils.

11. The method according to claim 1 wherein the biomaterial is molded, shaped, embossed and/or subjected to plastic compaction.

12. A polymeric collagen biomaterial obtained by the method according to claim 1.

13. A tissue equivalent implant comprising a biomaterial according to claim 12.

* * * * *